United States Patent
Pelster et al.

[11] Patent Number: 5,830,931
[45] Date of Patent: Nov. 3, 1998

[54] PROCESS FOR THE PREPARATION OF POLYCYCLIC COMPOUNDS

[75] Inventors: Thomas Pelster, Köln; Dietmar Kalz, Neunkirchen-Seelscheid, both of Germany

[73] Assignee: Bayer Aktiengesellschaft, Leverkusen, Germany

[21] Appl. No.: 767,733

[22] Filed: Dec. 16, 1996

[30] Foreign Application Priority Data

Dec. 22, 1995 [DE] Germany .................. 195 48 453.3

[51] Int. Cl.⁶ ................ C08K 5/3465; C07D 239/70
[52] U.S. Cl. ................ 524/90; 524/89; 544/245
[58] Field of Search ............. 544/245; 524/90, 524/89

[56] References Cited

U.S. PATENT DOCUMENTS

| | | |
|---|---|---|
| 3,819,632 | 6/1974 | Burdeska . |
| 3,833,583 | 9/1974 | Kalz et al. ................ 524/90 |
| 4,024,144 | 5/1977 | Geroll et al. ................ 524/90 |
| 4,097,450 | 6/1978 | Papenfuhs et al. ................ 524/90 |
| 4,417,014 | 11/1983 | Buecheler ................ 524/90 |
| 5,466,805 | 11/1995 | Roschger . |
| 5,530,130 | 6/1996 | Roschger et al. ................ 524/90 |

FOREIGN PATENT DOCUMENTS

| | | |
|---|---|---|
| 570800 | 11/1993 | European Pat. Off. . |
| 2157547 | 10/1971 | Germany . |
| 2236555 | 2/1974 | Germany . |
| 4327555 | 2/1995 | Germany . |
| 4339699 | 5/1995 | Germany . |
| 47-42750 | 12/1972 | Japan . |

OTHER PUBLICATIONS

Abstract of Belgian Patent 600,302.
Abstract of Japanese Patent 5-321,221.
Abstract of Japanese Patent JP 5-285,218.

*Primary Examiner*—Veronica P. Hoke
*Attorney, Agent, or Firm*—Sprung Kramer Schaefer & Briscoe

[57] ABSTRACT

Process for the preparation of compounds of the general formula (I)

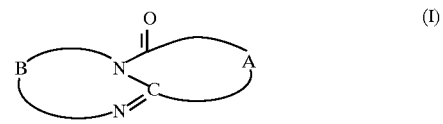

by reaction of aromatic dicarboxylic acids of the formula (II)

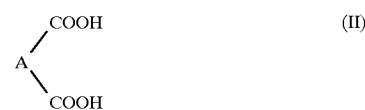

or anhydrides and/or esters thereof with aromatic diamines of the formula (III)

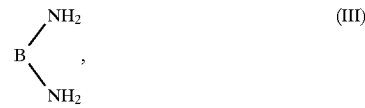

wherein A and B have the meaning given in the description, characterized in that the reaction of (II) with (III) is carried out in a reaction medium which comprises water and a hydrotropic compound which has a dielectric constant ε of 20 to 60 at 25° C.

14 Claims, No Drawings

PROCESS FOR THE PREPARATION OF POLYCYCLIC COMPOUNDS

The present invention relates to a new process for the preparation of polycyclic compounds and the use of the polycyclic compounds thus obtained for dyeing synthetic hydrophobic materials.

It is already known that polycyclic compounds, such as perinones, can be prepared from the corresponding aromatic dicarboxylic acids and diamines in various solvents and in the melt (DE-A-24 24 542, BE-A-600 302, DE-A-22 36 555, DE-A-21 57 547, DE-A-43 39 699, DE-A-43 27 555 and EP-A-570 800).

It is furthermore known from JP-A-53 21 221 to allow the preparation of such perinones to proceed in aqueous reaction media, such as aqueous hydrochloric acid, and in the presence of a nonionic or cationic surface-active agent. In JP-A-52 85 218, the reaction to give perinones is also carried out in an aqueous reaction medium comprising hydrochloric acid and a wetting agent. Alcohols, such as, for example, methanol, ethanol, isopropanol, ethylene glycol or glycerol, are mentioned as typical wetting agents. Although the organic reaction medium is replaced by an aqueous reaction medium in the process mentioned last, this does not lead to products in the desired purity. Thus, for example, the content of unreacted diamine and of organic residues, such as, for example, imides, which can be formed as by-products from the diamines and dicarboxylic acid derivatives employed and are insoluble in plastics, in the product obtained is too high, so that expensive subsequent purification steps are necessary before its further use.

A process has been found for the preparation of compounds of the formula (I)

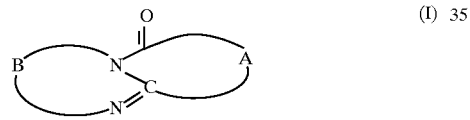

by reaction of aromatic di- or tetracarboxylic acids of the formula (II)

or anhydrides and/or esters thereof with aromatic diamines of the formula (III)

wherein
A and B independently of one another denote ortho-phenylene, ortho-naphthylene, peri-(1,8)-naphthylene or arylene of more than two benzene rings fused with one another, which is optionally substituted, where the arylene radicals A and B in formula (I) which contain more than two benzene rings fused with one another are bridged in the ortho-position or corresponding to a peri-position in the naphthylene, which is characterized in that the reaction of (II) and (III) is carried out in a reaction medium which comprises water and a hydrotropic compound which has a relative dielectric constant $\epsilon$ of 20 to 60, preferably 30–50 (at 25° C.).

The relative dielectric constant $\epsilon$ of a substance at a certain temperature is the ratio of the capacitance of a capacitor filled with the substance to the capacitance of the same capacitor in vacuo at this temperature (in this context, cf. also Lexikon der Physik [Dictionary of Physics], Volume 1, Hermann Franke, Franckhsche Verlagshandlung, Stuttgart 1969).

The peri-position actually corresponds to the 1,8-position in naphthalene. However, both in the literature and in the context of the present Application, the meaning is also extended to arylenes which contain more than two benzene rings fused with one another.

Examples of possible substituents for A are one or more identical or different substituents Y, where Y denotes $C_1$–$C_6$-alkyl, halogen, nitro, $C_6$–$C_{10}$-aryl, $C_6$–$C_{10}$-aryloxysulphonyl, hydroxyl, $C_1$–$C_4$-alkoxy, $C_6$–$C_{10}$-aryloxy, an aminosulphonyl which is optionally substituted by $C_1$–$C_6$-alkyl or $C_6$–$C_{10}$-aryl, or a fused-on cycloaliphatic or heterocyclic radical.

Particularly preferred substituents X are chlorine, fluorine, bromine, nitro, methoxy, $NH_2$, benzyloxy, hydroxyl, —$SO_2O(C_6H_5)$, —$SO_2N(CH_3)_2$, —$SO_2NHCH_3$, methyl, ethyl, n-propyl, iso-propyl, n-, sec- or tert-butyl, $NHCOCH_3$, —$N(C_2H_5)_2$ or optionally substituted phenyl.

Possible substituents for B are, for example, one or more identical or different substituents X, where X can assume the meaning of Y, but is independent of this.

In a preferred embodiment of the process according to the invention, compounds of the formula (I) which correspond to the formula (IV)

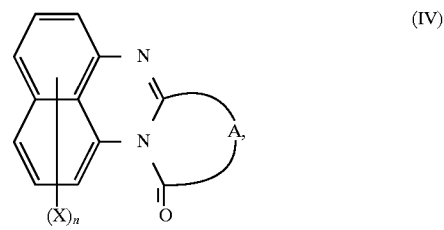

wherein
A and X have the abovementioned meanings and
n represents a number from zero to 6,
are prepared.

The compounds to be prepared according to the invention are preferably yellow to red or violet dyestuffs which are employed for dyeing synthetic fibre materials of, for example, polyester or polyvinyl materials, but in particular for bulk dyeing of plastics. These dyestuffs are particularly heat-stable and fast to light.

It is not necessary to employ one of the two compounds in excess for the condensation reaction of the compounds (II) and (III), and stoichiometric amounts are preferably used.

The starting compounds of the formula (II) and (III) and the functional derivatives of (II) in the form of the di- or tetracarboxylic acid anhydrides or $C_1$–$C_4$-alkyl esters, such as, for example, methyl or ethyl esters, are known or are obtainable by known methods. Preferred aromatic di- or tetracarboxylic acids of the formula (II) are phthalic acid, 3- or 4-chlorophthalic acid, dichlorophthalic acids, trichlorophthalic acids, tetrachlorophthalic acid, tetrabromophthalic acid, 3-methylphthalic acid, 3,5-dimethylphthalic acid, 4-methylphthalic acid, 4-phenoxyphthalic acid, 3-hydroxy-phthalic acid, 4-phenylphthalic acid, 4-phenylsulphonylphthalic acid, 3-benzoylphthalic acid, 4-nitrophthalic acid, 4-acetaminophthalic acid, 3-benzoylaminophthalic acid, 4-aminosulphonylphthalic acid, 4-phenoxysulphonylphthalic acid, 3-acetoxyphthalic acid, trimellitic acid, naphthalene-2,3-dicarboxylic acid, peri-naphthalene-1,8-dicarboxylic acid, 4-chloro-naphthalene-1,8-dicarboxylic acid, 4-phenylmercapto-naphthalene-1,8-dicarboxylic acid, 4,5-ethylene-naphthalene-1,8-dicarboxylic acid or anthracene-1,2-dicarboxylic acid or anhydrides or esters thereof.

Preferred aromatic diamines of the formula (III) are: o-phenylenediamine, chloro-o-phenylenediamines, dichloro-o-phenylenediamines, methyl-o-phenylenediamines, ethyl-o-phenylenediamines, methoxy-o-phenylenediamines, acetamino-o-phenylenediamines, phenyl-o-phenylenediamines or naphthylene-o-diamines, and furthermore 1,8-naphthylenediamine, chloro-1,8-naphthylenediamines, dichloro-1,8-naphthylenediamines, methyl-1,8-naphthylenediamines, dimethyl- 1,8-naphthylenediamines, methoxy-1,8-naphthylenediamines, ethoxy-1,8-naphthylenediamines, acetamino-1,8-naphthylenediamines and 1,8-diaminoacetnaphthylene.

In a particularly preferred process variant of the process according to the invention, an optionally substituted peri-naphthylenediamine is employed as the compound of the formula (III), in particular an unsubstituted 1,8-naphthylenediamine.

If the aromatic carboxylic acid II is a dicarboxylic acid or its derivative, the ratio of II to III is preferably 1 to 1.5, in particular 1 to 1.1.

The process according to the invention is in general carried out at temperatures from 50° to 160° C., preferably at 90° to 140° C. The reaction is in general carried out under normal pressure, but it can also be carried out under reduced or increased pressure, in particular under 1 to 20 bar. If it is carried out under increased pressure, reaction at temperatures from 105° to 160° C. is preferred.

In a preferred embodiment, the reaction medium additionally comprises an inorganic or organic acid.

Possible inorganic acids are, for example, HCl, $H_2SO_4$, $H_3PO_4$ or $H_2CO_3$, and possible organic acids are, for example: methanesulphonic acid, acetic acid, formic acid, propionic acid, lactic acid or glycolic acid. Hydrochloric acid or sulphuric acid is preferably employed.

The amount of acid is in general 0.1 to 20% by weight, based on the reaction medium.

The reaction medium preferably comprises 50 to 85% by weight of water, 0.5 to 20% by weight of the hydrotropic compound and, if appropriate, 0 to 20% by weight of further additives.

A hydrotropic compound is understood as meaning water-soluble compounds which increase the solubility of a compound in water. Preferred hydrotropic compounds have a water-solubility of more than 200 g/l at 30° C. and are capable of dissolving the compounds of the formula II and III in water at the reaction temperature.

Preferred possible hydrotropic compounds are lactams, lactones or mixtures thereof.

Lactams which may be mentioned are, for example, γ-butyrolactam, γ-valerolactam, ε-caprolactam and their N-substituted derivatives, such as N-methyl-γ-butyrolactam. Suitable lactones are, for example, γ-butyrolactone, γ-valerolactone and δ-valerolactone.

Preferred hydrotropic compounds are N-methyl-γ-butyrolactam, ε-caprolactam and γ-butyrolactone.

The hydrotropic compound is in general employed in an amount which is sufficient to dissolve the diamines III employed and/or the di- or tetracarboxylic acids or derivatives thereof II at the chosen reaction temperature. The hydrotropic compounds furthermore have the effect of significantly improving stirrability in highly concentrated batches. It is preferable to employ the hydrotropic compound in an amount of 0.5 to 20% by weight, based on the reaction medium, in particular 1 to 20% by weight.

The process according to the invention is as a rule carried out by preparing a solution of the starting substances with the aid of the hydrotropic compound, if appropriate adding an inorganic or organic acid, and heating the mixture to a temperature of 50° to 160° C.

The particular starting substances can also first be dissolved individually, preferably at least one of the solutions being aqueous, and the solutions can then be combined.

When the reaction has ended, the product is filtered off and preferably washed with water or an aqueous mixture which corresponds to the reaction medium in composition, and dried.

The compounds of the formula (I) thus obtained as a rule are formed with a yield of 90 to 98%. They have a content of unreacted diamine III of less than 500 ppm in the solid.

The reaction is preferably carried out in an inert gas atmosphere.

The dyestuffs prepared by the process according to the invention are employed for dyeing synthetic hydrophobic fibre materials, such as cellulose triacetate, polyethylene terephthalate or polyamides, by known dyeing processes, but in particular for spin dyeing and bulk dyeing of thermoplastics, such as polystyrene, polyester, polycarbonate and copolymers, such as acrylonitrile/butadiene/styrene, styrene/acrylonitrile and the like.

Bulk dyeing here is understood as meaning, in particular, processes in which the dyestuff is incorporated into the molten mass of plastic, for example with the aid of an extruder, or in which the dyestuff is added to starting components for the preparation of the plastic, for example monomers, even before the polymerization.

Particularly preferred plastics are thermoplastics, for example vinyl polymers, polyesters and polyamides.

Suitable vinyl polymers are polystyrene, styrene/acrylonitrile copolymers, styrene/butadiene copolymers, styrene/butadiene/acrylonitrile terpolymers, polymethacrylate and others.

Other suitable polyesters are: polyethylene terephthalates, polycarbonates and cellulose ethers.

Polystyrene, styrene copolymers, polycarbonates and polymethacrylate are preferred. Polystyrene is particularly preferred.

The high molecular weight compounds mentioned can be present as plastic compositions or melts individually or in mixtures.

The dyestuffs according to the invention are converted into finely divided form for use, it being possible but not necessary also to use dispersing agents.

If the dyestuffs (I) are employed after the polymerization, they are mixed or ground with the granules of plastic in the dry state and this mixture is plasticized and homogenized, for example on mixing rolls or in extruders. However, the dye-stuffs can also be added to the molten material and distributed homogeneously by stirring. The material predyed in this way is then further processed in the customary manner, for example by spinning to bristles, filaments and the like or by extrusion or in the injection moulding process to give mouldings.

The dyestuffs of the formula (I) are preferably employed for dyeing the polymers mentioned in amounts of 0.0001 to 1% by weight, in particular 0.01 to 0.5% by weight, based on the amount of polymer.

Corresponding valuable opaque dyeings can be obtained by addition of pigments which are insoluble in the polymers, such as, for example, titanium dioxide.

Titanium dioxide can be used in an amount of 0.01 to 10% by weight, preferably 0.1 to 5% by weight based on the amount of polymer.

Transparent or opaque dyeings of good heat stability and good fastness to light and weathering are obtained by the process according to the invention.

The invention also relates to plastics comprising at least one dyestuff which has been obtained by the preparation process according to the invention.

EXAMPLES

Example 1

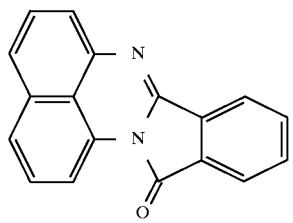

350 ml of 5% strength aqueous sulphuric acid were added to a mixture of 31.6 g (0.2 mol) of 1,8-diaminonaphthalene, 35 g of ε-caprolactam and 29.6 g (0.2 mol) of phthalic anhydride and the mixture was heated to 80° C. After 1 hour, the temperature was increased to 90° to 95° C. and maintained for 7 hours. When the reaction had ended, the orange precipitate was filtered off hot and washed with water and methanol. 53 g (98% of theory) of the above dyestuff were obtained. The amine content was determined by means of HPLC (<500 ppm). 100 ml of xylene were added to 1 g of the dyestuff and the mixture was heated at 115° C. for 30 minutes. After filtration over a membrane filter, a residue on the filter of significantly less than 1% was found.

Example 2

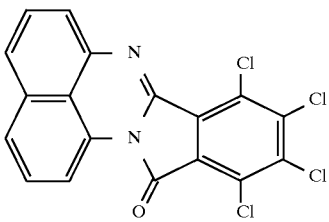

390 ml of 10% strength aqueous sulphuric acid were added to a solution of 39 g of N-methyl-γ-butyrolactam and 25.3 g (0.16 mol) of 1,8-diaminonaphthalene under an inert gas atmosphere and the mixture was stirred for 30 minutes. 45.7 g (0.16 mol) of tetrachlorophthalic anhydride were then metered in and the reaction mixture was heated at 130° C. in an autoclave for 8 hours (pressure: 4 bar). When the reaction had ended, the red dyestuff formed was filtered off hot and washed with water. 63.3 g (97% of theory) of the above dyestuff were obtained. The amine content, determined by HPLC, was below 500 ppm. 200 ml of xylene were added to 1 g of the dyestuff and the mixture was heated at 115° C. for 30 minutes. After filtration over a membrane filter, a residue on the filter of significantly <1% was found.

Example 3

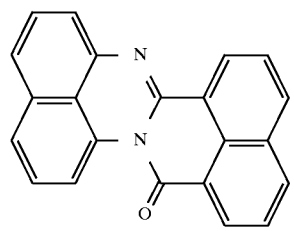

A solution of 19.8 g (0.1 mol) of naphthalic anhydride in 25 g of concentrated sulphuric acid was added to a mixture of 15.8 g (0.1 mol) of 1,8-diaminonaphthalene, 25 g of N-methyl-γ-butyrolactam and 250 ml of water under a nitrogen atmosphere, and the mixture was heated at 150° C. in an autoclave for 8 hours. The dyestuff formed was filtered off and washed with water. 31.4 g (98% of theory) of the above dyestuff were obtained. The amine content was determined by means of HPLC as <500 ppm. 100 ml of xylene were added to 1 g of the dyestuff and the mixture was heated at 115° C. for 30 minutes. After filtration over a membrane filter, a residue on the filter of significantly less than 1% was found.

Example 4

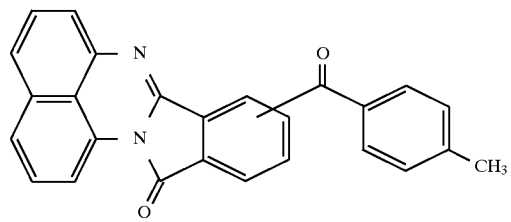

A solution of 15.8 g (0.1 mol) of 1,8-diaminonaphthalene in 25 g of N-methyl-γ-butyrolactam was added to a mixture of 250 ml of 5% strength aqueous sulphuric acid and 28.4 g (0.1 mol) of 4-(p-toluene)phthalic acid under a nitrogen atmosphere, and the mixture was heated to 140° C. in an autoclave and the temperature maintained for 7 hours. When the reaction had ended, the product was filtered off hot with suction and washed with a 10% strength aqueous N-methyl-γ-butyrolactam solution and then with water. 35.5 g (90% of theory) of the above dyestuff were obtained. The amine content was determined by means of HPLC as <500 ppm. 100 ml of xylene were added to 1 g of the dyestuff and the mixture was heated at 115° C. for 30 minutes. After filtration over a membrane filter, a residue on the filter of significantly less than 1% was found.

Example 5

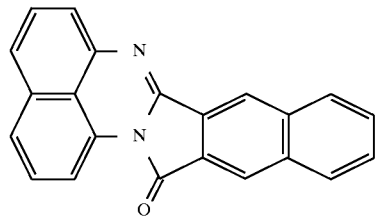

A mixture of 300 ml of 6% strength aqueous hydrochloric acid, 15.8 g (0.1 mol) of 1,8-diaminonaphthalene, 21.6 g (0.1 mol) of 2,3-naphthalenedicarboxylic acid and 40 g of γ-butyrolactone was heated at 140° C. for 7 hours. When the reaction had ended, the dyestuff was filtered off and washed with water. 31.1 g of the above dyestuff (≈97% of theory) were obtained. The amine content, determined by HPLC, was found to be <500 ppm. The residue on the filter, determined as in Example 1, was significantly <1%.

Example 6

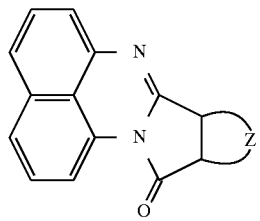

wherein Z=radical to complete a 1,2-naphthylene ring.

300 ml of a 5% strength aqueous methanesulphonic acid solution were added to a solution of 15.8 g (0.1 mol) of 1,8-diaminonaphthalene and 21.6 g (0.1 mol) of 1,2-naphthalenedicarboxylic acid in 40 g of γ-valerolactam under a nitrogen atmosphere, and the mixture was heated to 145° C. in an autoclave and stirred at this temperature for 8 hours. The dyestuff formed was filtered off hot with suction and washed with water. 31 g (97% of theory) of the above dyestuff were obtained. The amine content, determined by means of HPLC, was less than 500 ppm. The residue on the filter, determined as in Example 1, was <1%.

Examples 7–14

Dyestuffs were obtained in similarly good yields by reaction of the following diamines and dicarboxylic acid derivatives, analogously to the preceding examples:

| Ex. | Diamine | Phthalic acid derivative | Colour Shade |
|---|---|---|---|
| 7 | | | red |
| 8 | | R = Alkyl | red |
| 9 | | R = Alkyl | red |
| 10 | | | yellow |
| 11 | | X = NHR | yellow-orange |

| Ex. | Diamine | Phthalic acid derivative | Colour Shade |
|---|---|---|---|
| 12 | o-phenylenediamine (NH2, NH2) | naphthalene-1,8-dicarboxylic anhydride with X = COOR, R = Alkyl at 4,5-positions | yellow-orange |
| 13 | o-phenylenediamine (NH2, NH2) | naphthalene-1,8-dicarboxylic anhydride with X = 3,5-dimethylpyrazol-1-yl (N—N, H3C, CH3) at 4,5-positions | yellow-orange |
| 14 | 1,8-diaminonaphthalene (NH2, NH2) | naphthalene-1,8-dicarboxylic anhydride with NHCH3 substituent | red |

Comparison Example 1

Example 2 from patent specification JA 5 285 218 was reworked.

15.8 g (0.1 mol) of 1,8-diaminonaphthalene, 28.6 g (0.1 mol) of tetrachlorophthalic anhydride, 20 g of ethylene glycol and 400 ml of 10% strength aqueous hydrochloric acid were heated under reflux in a glass flask for 8 hours. After filtration, the filter cake was washed thoroughly with water. The resulting dyestuff (38 g) had a purity of only 85% (HPLC). 1 g of the crude dyestuff was heated in 200 ml of xylene at 115° C. for 30 minutes. After filtration over a membrane filter, a residue of 11%, based on the amount weighed out, was found.

Comparison Example 2

Example 1 from patent specification JA 5 321 221 was reworked.

15.8 g (0.1 mol) of 1,8-diaminonaphthalene, 14.8 g (0.1 mol) of phthalic anhydride, 350 g of 1.2% strength aqueous hydrochloric acid and 0.2 g of a nonionic surfactant were heated under reflux in a glass flask for 8 hours, After filtration, the filter cake was washed thoroughly with water. The resulting dyestuff (25 g) had a purity of only 80% (HPLC). 1 g of the crude dyestuff was heated in 100 ml of xylene at 115° C. for 30 minutes. After filtration over a membrane filter, a residue of 15%, based on the amount weighed out, was found.

We claim:

1. A process for the preparation of compounds of the formula

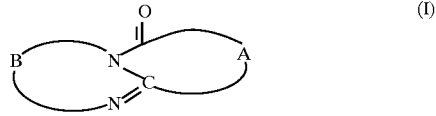

(I)

said process comprises reacting aromatic di- or tetracarboxylic acids of the formula

(II)

or anhydrides and/or esters thereof with aromatic diamines of the formula

(III)

wherein
A=ortho-phenylene, ortho-naphthylene, peri-(1,8)-naphthylene or arylene of more than two benzene rings fused with one another, which is unsubstituted or substituted, and
B=ortho-phenylene, ortho-naphthylene, peri-(1,8)-naphthylene or arylene of more than two benzene rings fused with one another, which is unsubstituted or substituted,
where the arylene radicals A and B in formula (I) which contain more than two benzene rings fused with one another are bridged in the ortho-position or corresponding to a peri-position in naphthalene, wherein the reaction of (II) with (III) is carried out in a reaction medium which comprises water, an inorganic or organic acid and 0.1 to 20% by weight, based on the reaction medium, of a hydrotropic compound or mixture of several hydrotropic compounds wherein the hydrotropic compound is a lactam, lactone or amide and the hydrotropic compound has a relative dielectric constant $\epsilon$ of 20 to 60 (at 25°) and the reaction temperature is from 50° C. to 160° C.

2. The process according to claim 1, wherein the compound is formed is

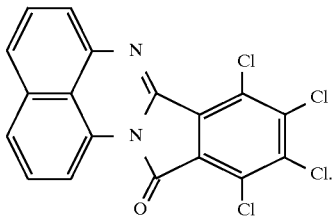

3. The process according to claim 2, wherein the acid employed is $H_2SO_4$ and the hydrotropic compound is a lactam.

4. A process for dyeing hydrophobic materials comprising adding a dyestuff prepared according to claim 1 to synthetic hydrophobic material.

5. A process for bulk dyeing of plastics comprising incorporating a dyestuff obtained by the process according to claim 1 into a molten mass of plastic or to the starting components for preparation of the plastic before the polymerization.

6. Plastics prepared according to the process of claim 5.

7. A process according to claim 1, wherein the substituents for A or B include one or more identical or different $C_1$–$C_6$-alkyl, halogen, nitro, $C_6$–$C_{10}$-aryl, $C_6$–$C_{10}$-aryloxysulphonyl, hydroxyl, $C_1$–$C_4$-alkoxy, $C_6$–$C_{10}$-aryloxy, an aminosulphonyl which is optionally substituted by $C_1$–$C_6$-alkyl or $C_6$–$C_{10}$-aryl, or a fused-on cycloaliphatic or heterocyclic radical.

8. A process according to claim 7, wherein the substituents represent chlorine, fluorine, bromine, nitro, methoxy, $NH_2$, benzyloxy, hydroxyl, —$SO_2O(C_6H_5)$, —$SO_2NHCH_3$, methyl, ethyl, n-propyl, iso-propyl, n-, sec- or tert-butyl, $NHCOCH_3$, —$N(C_2H_5)_2$ or optionally substituted phenyl.

9. A process according to claim 1, wherein the aromatic di- or tetracarboxylic acids of the formula (II) are phthalic acid, 3- or 4-chlorophthalic acid, dichlorophthalic acids, trichlorophthalic acids, tetrachlorophthalic acid, tetrabromophthalic acid, 3-methylphthalic acid, 3,5-dimethylphthalic acid, 4-methylphthalic acid, 4-phenoxyphthalic acid, 3-hydroxy-phthalic acid, 4-phenylphthalic acid, 4-phenylsulphonylphthalic acid, 3-benzoylphthalic acid, 4-nitrophthalic acid, 4-acetaminophthalic acid, 3-benzoylaminophthalic acid, 4-aminosulphonylphthalic acid, 4-phenoxysulphonylphthalic acid, 3-acetoxyphthalic acid, trimellitic acid, naphthalene-2,3-dicarboxylic acid, peri-napthalene-1,8-dicarboxylic acid, 4-chloro-naphthalene-1,8-dicarboxylic acid, 4-phenylmercapto-naphthalene-1,8-dicarboxylic acid, 4,5-ethylene-naphthalene-1,8-dicarboxylic acid, anthracene-1,2-dicarboxylic acid or anhydrides or $C_1$–$C_4$-alkyl esters thereof which can be substituted or unsubstituted.

10. A process according to claim 1, wherein the hydrotropic compounds are lactams, lactones or mixtures thereof.

11. A process according to claim 1, wherein the lactams are γ-butyrolactam, γ-valerolactam, ε-caprolactam and their N-substituted derivatives and the lactones are γ-butyrolactone, γ-valerolactone and δ-valerolactone.

12. A process according to claim 1, wherein the hydroprotic compounds are N-methyl-γ-butyrolactam, ε-caprolactam and γ-butyrolactone.

13. A process according to claim 1, wherein the reaction medium comprises from about 50% to 85% by weight water.

14. A process according to claim 1, wherein the aromatic diamines of the formula (II) are o-phenylenediamine, chloro-o-phenylenediamines, dichloro-o-phenylenediamines, methyl-o-phenylenediamines, ethyl-o-phenylenediamines, methoxy-o-phenylenediamines, acetamino-o-phenylenediamines, phenyl-o-phenylenediamines or naphthylene-o-diamines, and furthermore 1,8-naphthylenediamine, chloro-1,8-naphthylenediamines, dichloro-1,8-naphthylenediamines, methyl-1,8-naphthylenediamines, dimethyl-1,8-naphthylenediamines, methoxy-1,8-naphthylenediamines, ethoxy-1,8-naphthylenediamines, acetamino-1,8-naphthylenediamines and 1,8-diaminoacetnaphthytene.

* * * * *

UNITED STATES PATENT AND TRADEMARK OFFICE
CERTIFICATE OF CORRECTION

PATENT NO. : 5, 830, 931
DATED : November 3, 1998
INVENTOR(S) : Thomas Pelster, et al.

It is certified that error appears in the above-identified patent and that said Letters Patent is hereby corrected as shown below:

Title Page, [56], References Cited,                Delete "Geroll" and substitute
U.S. Patent Documents, line 3                      --Groll--

Signed and Sealed this

Twenty-fourth Day of August, 1999

Attest:

Q. TODD DICKINSON

*Attesting Officer*       *Acting Commissioner of Patents and Trademarks*